(12) United States Patent
Van Helfteren et al.

(10) Patent No.: US 11,179,548 B2
(45) Date of Patent: Nov. 23, 2021

(54) DEVICE FOR THE DISPLACEMENT OF A HOLLOW ORGAN OF A PATIENT

(71) Applicant: MEDFACT Engineering GMBH, Lorrach (DE)

(72) Inventors: Alwin Van Helfteren, Mullheim-Feldberg (DE); Jorg Reinhardt, Grenzach-Wyhlen (DE)

(73) Assignee: MEDFACT ENGINEERING GMBH, Lorrach (DE)

( * ) Notice: Subject to any disclaimer, the term of this patent is extended or adjusted under 35 U.S.C. 154(b) by 506 days.

(21) Appl. No.: 15/555,852

(22) PCT Filed: Feb. 23, 2016

(86) PCT No.: PCT/IB2016/050954
§ 371 (c)(1),
(2) Date: Sep. 5, 2017

(87) PCT Pub. No.: WO2016/139552
PCT Pub. Date: Sep. 9, 2016

(65) Prior Publication Data
US 2018/0042691 A1    Feb. 15, 2018

(30) Foreign Application Priority Data

Mar. 5, 2015   (DE) .................. 102015103213.9

(51) Int. Cl.
*A61M 25/10*   (2013.01)
*A61M 29/02*   (2006.01)
(Continued)

(52) U.S. Cl.
CPC ..... *A61M 25/1011* (2013.01); *A61B 18/1492* (2013.01); *A61B 90/04* (2016.02);
(Continued)

(58) Field of Classification Search
CPC ................ A61B 90/04; A61B 18/1492; A61B 2090/0427; A61B 2018/00351;
(Continued)

(56) References Cited

U.S. PATENT DOCUMENTS 5,090,958 A * 2/1992 Sahota .............. A61M 25/1002
600/585
5,295,960 A * 3/1994 Aliahmad ............. A61M 25/10
604/103
5,395,333 A * 3/1995 Brill ................... A61M 25/1011
604/101.05
(Continued)

FOREIGN PATENT DOCUMENTS

JP    2003-250896    *  2/2002

OTHER PUBLICATIONS

Machine Translation of JP 2003-250896, Retrieved Mar. 23, 2020, pp. 1-5.*

*Primary Examiner* — Jing Rui Ou
(74) *Attorney, Agent, or Firm* — Tarolli, Sundheim, Covell & Tummino LLP

(57) ABSTRACT

The invention relates to a balloon catheter (1), which allows esophageal injuries to be prevented by the displacement of the esophagus of a patient during catheter ablation for cardiac arrhythmias. For this purpose, three balloons (7, 9, 11) are provided along a catheter shaft (3), which are arranged at a distance from each other and can each be alternately expanded in opposite directions.

11 Claims, 5 Drawing Sheets

(51) Int. Cl.
 *A61B 90/00* (2016.01)
 *A61B 18/14* (2006.01)
 *A61B 18/00* (2006.01)

(52) U.S. Cl.
 CPC ........ *A61M 25/1002* (2013.01); *A61M 29/02* (2013.01); *A61B 2018/00351* (2013.01); *A61B 2018/00577* (2013.01); *A61B 2090/0427* (2016.02); *A61M 2210/105* (2013.01)

(58) Field of Classification Search
 CPC .... A61B 2018/00577; A61M 25/1002; A61M 25/1011; A61M 29/02; A61M 2210/105
 See application file for complete search history.

(56) References Cited

U.S. PATENT DOCUMENTS

| | | | | |
|---|---|---|---|---|
| 5,766,151 A | * | 6/1998 | Valley | A61M 25/0155 604/103.07 |
| 6,010,479 A | * | 1/2000 | Dimitri | A61J 15/0015 604/525 |
| 2002/0072706 A1 | * | 6/2002 | Hiblar | A61M 25/0084 604/101.01 |
| 2002/0143237 A1 | * | 10/2002 | Oneda | A61B 1/00082 600/116 |
| 2003/0171741 A1 | * | 9/2003 | Ziebol | A61B 18/245 606/7 |
| 2003/0176758 A1 | * | 9/2003 | Nakano | A61M 25/1027 600/3 |
| 2006/0129093 A1 | * | 6/2006 | Jackson | A61M 25/1011 604/96.01 |
| 2006/0178691 A1 | * | 8/2006 | Binmoeller | A61F 5/0079 606/191 |
| 2008/0051758 A1 | * | 2/2008 | Rioux | A61B 17/12022 604/509 |
| 2008/0249463 A1 | * | 10/2008 | Pappone | A61M 25/1011 604/101.05 |
| 2010/0152717 A1 | * | 6/2010 | Keeler | A61B 18/24 606/7 |
| 2011/0082488 A1 | * | 4/2011 | Niazi | A61M 25/1002 606/192 |
| 2014/0277319 A1 | * | 9/2014 | Osypka | A61M 25/1002 607/116 |

* cited by examiner

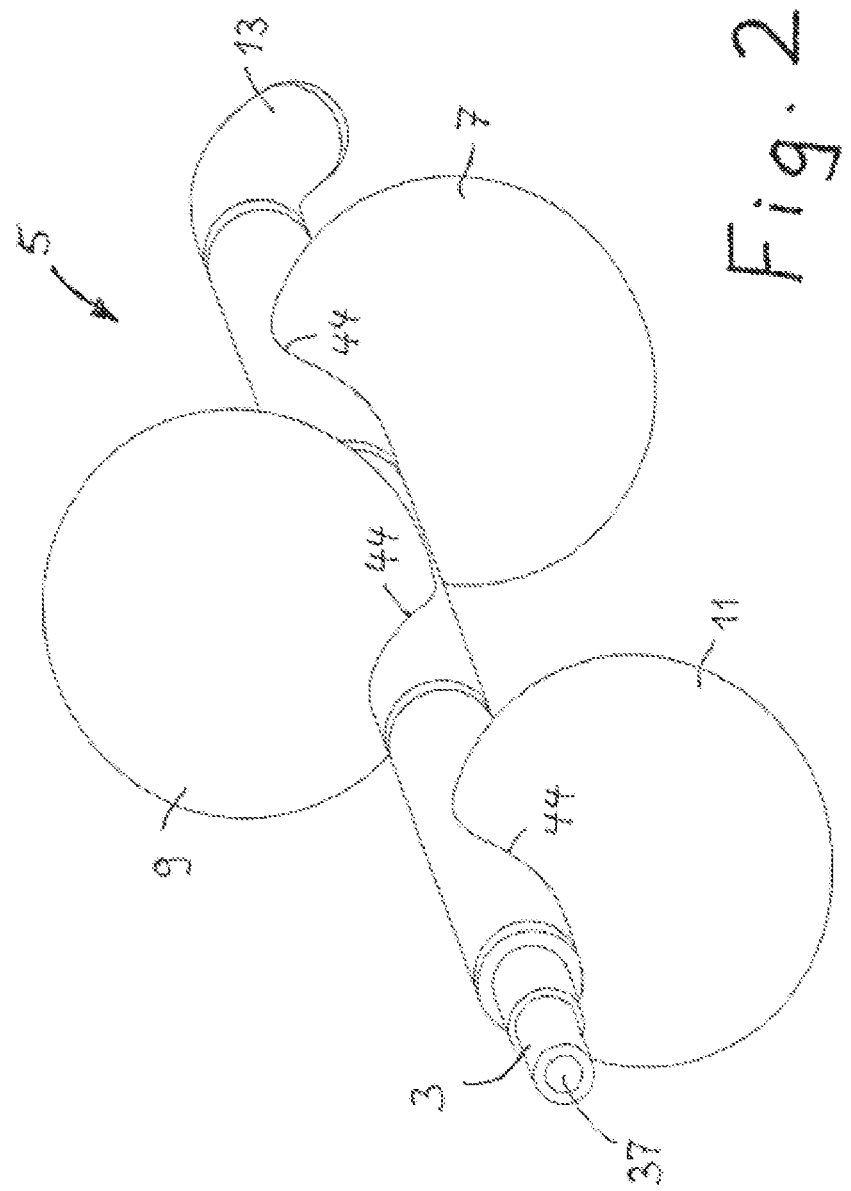

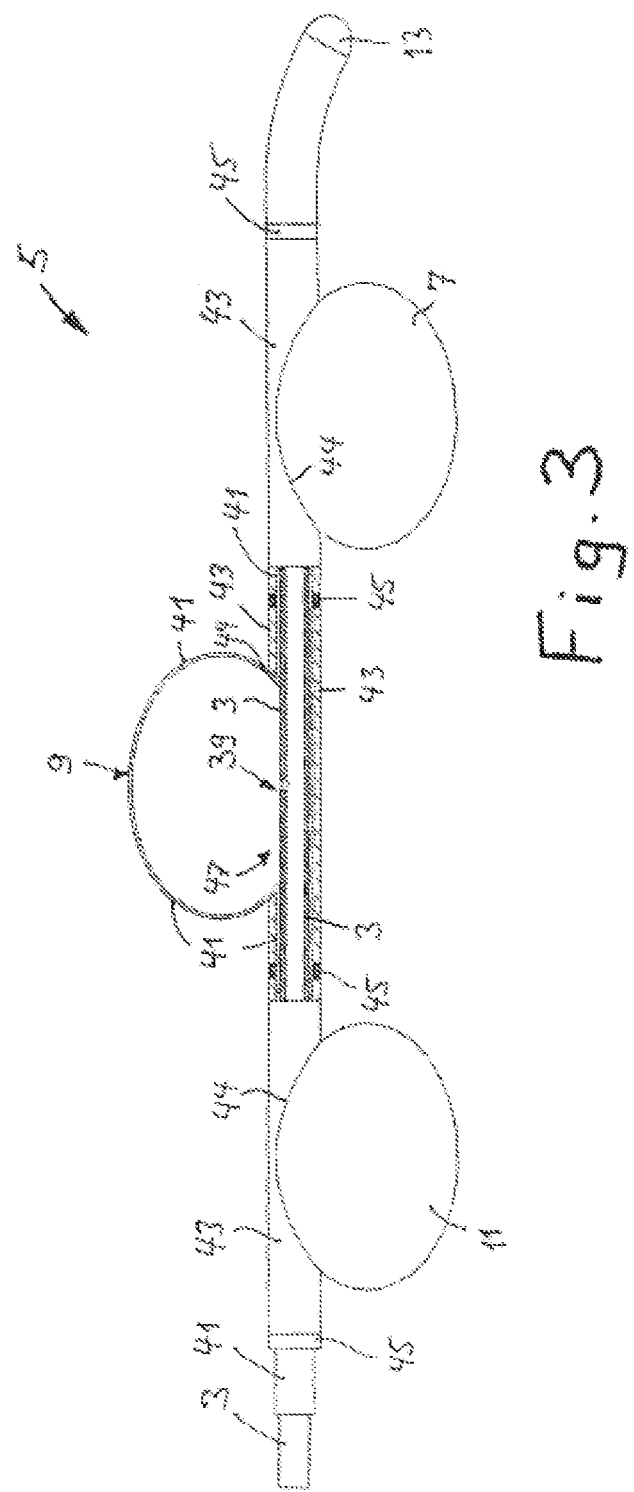

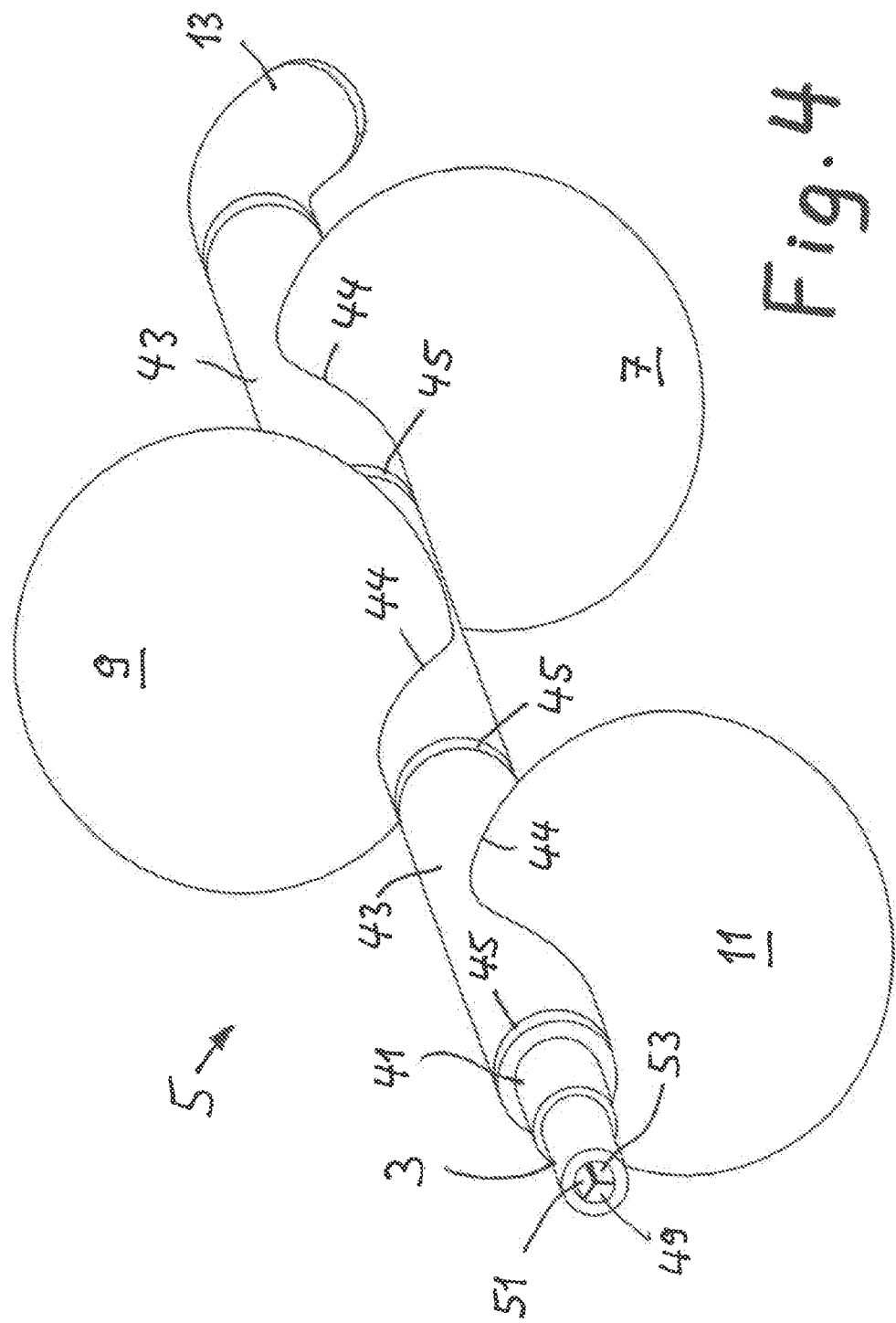

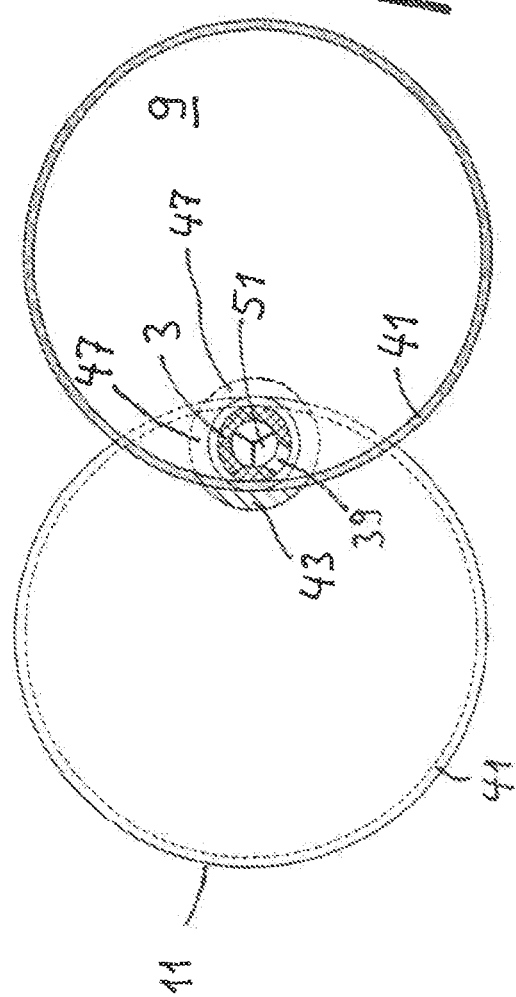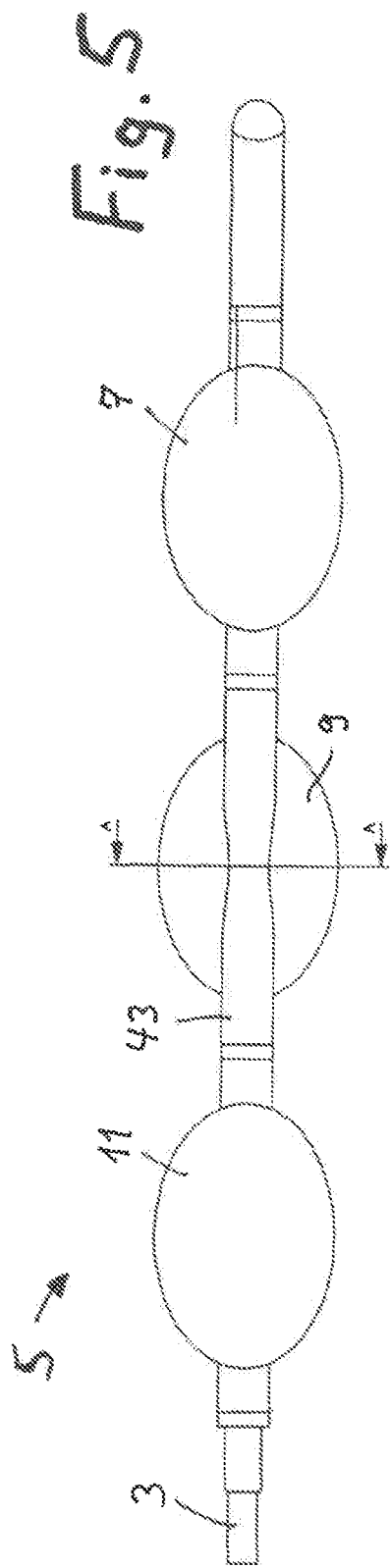

DEVICE FOR THE DISPLACEMENT OF A HOLLOW ORGAN OF A PATIENT

The invention relates to a device for displacing a hollow organ of a patient, in particular the esophagus during catheter ablation for cardiac arrhythmias to avoid esophageal injuries, comprising a balloon system that can be asymmetrically expanded in the hollow organ so as to exert displacement pressure on the inner side of the hollow organ, and comprising a catheter shaft, which is connected to the expandable balloon system and by way of which the asymmetrical expansion of the balloon system can be controlled using a filling medium.

At the 80th Annual Conference of the Deutsche Gesellschaft für Kardiologie-, Herz- und Kreislaufforschung e.V. (German Association for Cardiology, Heart and Circulatory Research) in Mannheim on Apr. 23 to 26, 2014, Heiko Lehrmann et al. presented a method in which the esophagus is displaced during pulmonary vein isolation by way of cryo technology using a transesophageal echocardiography (TEE) probe.

U.S. Pat. No. 5,170,803 describes a device and a method for displacing the esophagus in front of the heart.

All previously described devices, however, have the disadvantage that the force to be exerted on the esophagus for displacement takes place by applying pressure onto a comparatively small surface.

So as to distribute the force required for the displacement onto the esophagus. US patent application US 2011/0082488 A1 provides an asymmetrically expandable balloon catheter. To generate asymmetry, the elongate balloon is provided with a strip, which is less flexible than the flexible material of the balloon and thereby brings about stiffening on one side, so that the balloon flexes during expansion and bends the esophagus away from the region of the left atrium of a heart.

It is the object of the invention to provide a device for displacing a hollow organ, in particular the esophagus, which can be used in a well-controlled manner and with high precision.

According to the invention, this object is achieved in that, in a device of the type mentioned at the outset, the expandable balloon system comprises at least one balloon disposed transversally to the catheter shaft.

In an expedient exemplary embodiment of the invention, multiple balloons extending transversally to the catheter shaft are provided. The balloons can be expanded independently of one another via a single lumen present in the catheter shaft, or via individually associated separate lumina, by introducing the filling medium.

It is expedient when three balloons are disposed spaced equidistantly apart from one another in the axial direction. The balloons are preferably disposed laterally with respect to the longitudinal direction, pointing in different directions.

To achieve good control, it is advantageous when the balloons are disposed along the longitudinal axis of the balloon system so as to alternately point radially in opposite directions.

In a preferred exemplary embodiment, the catheter shaft has a lateral passage, which is surrounded by an elastic balloon tube and a covering tube in the balloon region. In the vicinity of the passage, the covering tube has a cut-out, so that it is possible, with the aid of a filling medium introduced through the catheter shaft and the passage, to achieve an expansion of the balloon tube inside the cut-out for forming a balloon, so that the desired displacement can take place with high precision by varying the pressure of the fluid that is used.

A simple mechanical design is obtained when the covering tube has a distal cut-out, an intermediate cut-out and a proximal cut-out. These cut-outs are disposed along the longitudinal axis of the catheter shaft, alternately pointing in opposite directions.

If a separate activation of the balloon for particularly good control of the displacement is desired, it is expedient when the catheter shaft has three lumina, which are each connected via a separate feed line to a syringe or a pump so as to control the dilation of the individual balloons in such a way that optimal curvature of the hollow organ, particularly the esophagus, is obtained.

In a preferred exemplary embodiment, the balloon system is surrounded by an outer elastic balloon tube, so as to be accessible for easier cleaning and achieve an improved visual impression.

Exemplary embodiments of the invention will be described hereafter in greater detail based on drawing. In the drawings:

FIG. 2 shows an enlarged schematic view of a balloon system according to one exemplary embodiment of the invention;

FIG. 3 shows the balloon system according to FIG. 2 in a partially cut side view;

FIG. 4 shows a further exemplary embodiment of the invention in which a separate dilation of each balloon is possible, deviating from the exemplary embodiment shown in FIG. 2;

FIG. 5 shows a view of the balloon system in the direction of the plane spanned by the balloons; and FIG. 6 shows a sectional view along line A-A in FIG. 5 to illustrate the formation of the balloon by the expansion of a balloon tube through a cut-out in a covering tube when a fluid is pressed in via a passage in the wall of the catheter shaft.

Figure 1:
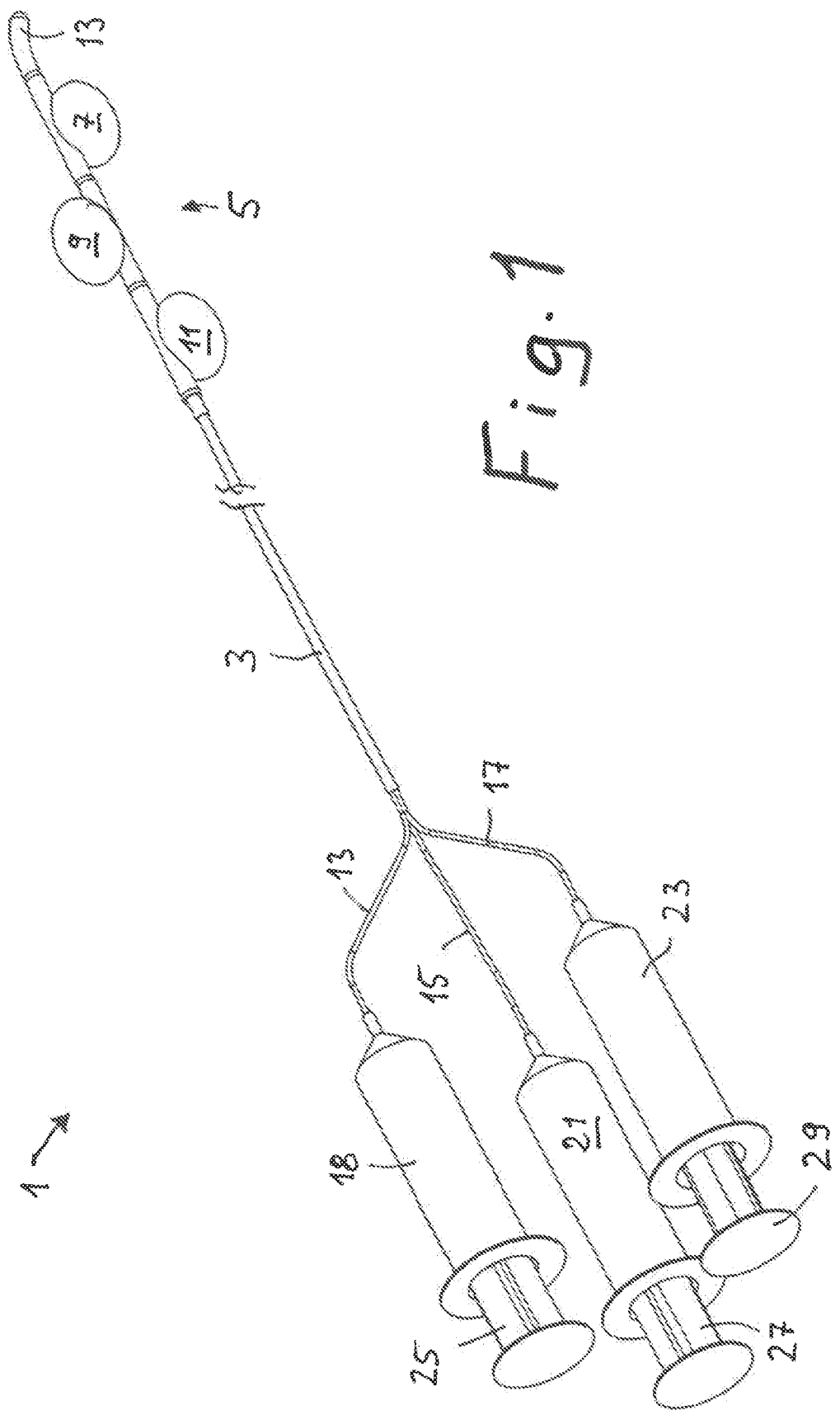
FIG. 1 shows an exemplary embodiment of the invention in a perspective schematic overall view.

In the perspective view of FIG. 1, a balloon catheter 1 comprising a catheter shaft 3, which for illustrative purposes is shown shortened and interrupted, and a balloon system 5 can be seen. The balloon system 5 comprises a distal balloon 7, an intermediate balloon 9 and a proximal balloon 11. The balloons 7, 9 and 11 protruding laterally from the catheter shaft 3 are disposed equidistantly from one another along the longitudinal axis of the balloon system 5, wherein in the position shown in FIG. 1 the distal balloon 7 and the proximal balloon 11 extend downwardly, and the intermediate balloon 9 extends upwardly in the opposite direction transversally to the catheter shaft 3. The distal balloon 7 is located in the vicinity of the distal end 13 of the balloon catheter 1, which can preferably be slightly curved to facilitate insertion via the nose or the mouth to the esophagus of a patient. The curvature 13 preferably points in the same direction as the two parallel oriented balloons 7 and 11 so as to facilitate anatomically correct positioning.

In the first exemplary embodiment of the invention shown in FIG. 1, respective separate lumina in the catheter shaft 3 are associated with the distal balloon 7, the intermediate balloon 9 for pushing the esophagus away from the heart, and the proximal balloon 11. The three lumina of the catheter shaft 3 are connected to syringes 18, 21 and 23 via feed lines 16, 15 and 17, which are each associated with the balloons 7, 9 and 11 and appropriately labeled. The syringes 18, 21, 23 having volumes of 60 to 120 ml allow a fluid, such as air or a liquid, to be delivered as the filling medium into the respectively associated balloons 7, 9 and 11 so as to expand these to a balloon diameter of approximately 10 to 60 mm.

In an expedient exemplary embodiment, the feed lines 13, 16 and 17 are each connected via shut-off valves (such as a Luer Lock system), which are not shown, to the syringes 18, 21, 23, which can be closed after the balloons 7, 9 and 10 have been expanded so as to maintain the expansion of the balloons 7, 9 and 11. The shut-off valves are opened, and the plungers 25, 27 and 29 are pushed out or pulled out, to collapse the balloons.

Instead of using syringes 18, 21, 23, it is also possible to use other means, such as pumps, to control the dilation of the balloons 7, 9 and 11.

FIG. 2 shows an exemplary embodiment of a balloon system 5, in which the catheter shaft 3 has a single lumen 37, by way of which the three fully expanded balloons 7, 9 and 11 are connected to a single syringe, which is not shown in the drawing, and can thus be jointly expanded with the aid of the same.

The configuration of the balloon system 5 shown in a perspective view in FIG. 2 is shown in a partially cut view in FIG. 3. The catheter shaft 3 is provided with a respective passage 39 in the region of the balloons 7, 9 and 11. When a filling medium is pressed in with the aid of a syringe having a volume between 50 ml and 500 ml, this filling medium finds its way via the catheter shaft 3 and the passage 39 into the interior of the balloon 9, wherein the amount of filling medium introduced with the aid of a syringe or another pump and the respective pressure conditions define the extent to which a balloon expansion takes place.

The balloons 7, 9 and 11 are preferably formed by the expansion of a balloon tube 41 extending in the longitudinal direction of the balloon system 5 around the catheter shaft 3. For this purpose, as is illustrated in FIG. 3, the balloon tube 41 is surrounded by a covering tube 43 in which at least one cut-out 47 is provided, which allows the balloon tube 41 to be widened only in the region of the cut-out 47.

For forming the balloons 7, 9, 11, the covering tube 43 is, or the segments of the covering tube 43 are, provided with respective cut-outs 47 disposed at a distance from one another along the catheter shaft, which extend across the provided balloon length in the axial direction and in the circumferential direction across approximately half the circumference with a curved boundary line 44 in such a way that the balloon tube 41 bulges in a manner similar to a hernia when the fluid is introduced at a pressure through one of the passages 39, since the wall formed by the covering tube 43 is more stable than the elastic balloon tube 41, which is made of silicone, latex, PUR, chronoprene or C-Flex, for example.

The covering tube 43 can be designed as one piece or as multiple pieces, wherein rings 45 can be provided between individual segments of the covering tube 43, which can be provided for marking under X-rays, or can assume a function for sealingly pressing the balloon tube 41 onto the catheter shaft 3. So as to seal the individual balloons 7, 9 and 11, it may be expedient to seal the covering tube 43 and the balloon tube 41, for example by bonding the regions of the balloon tube 41 between the locations at which balloons are to be formed. It is also possible to wrap the regions to be sealed along the catheter shaft 3 so as to achieve sealing.

In the exemplary embodiment according to FIGS. 2 and 3, the catheter shaft 3 has a single lumen, while in the exemplary embodiment of the invention described based on FIG. 1 the catheter shaft 3 comprises three separate lumina 49, 51 and 53, as is illustrated in FIG. 4. Each of these lumina 49, 51, 53 opens via separate passages 39 into only one of the balloons 7, 9, 11, so that these balloons 7, 9, 11 can each be expanded independently of one another so as to be able to adapt the pressing forces well to the respective conditions in a hollow organ, in particular the esophagus.

FIG. 5 illustrates a top view onto the balloon system 5 after the balloons 7, 9 and 11 have been expanded. For illustration purposes, FIG. 6 shows a sectional view through the balloon 9 along line A-A in FIG. 5. The intermediate balloon 9 is expanded by the introduction of a fluid through the lumen 51 of the catheter shaft 3 and the passage 39. After being expanded to form the balloon 9, the balloon tube 41 approximately has the shape schematically illustrated in FIG. 6 and protrudes through the cut-out 47 in the covering tube 43, while the covering tube 43, outside the cut-out 47, is dimensioned in such a way that the balloon tube 41 is prevented from expanding.

It is expedient when all parts of the balloon system 5, except for those used for marking, are made of plastic material that is transparent to X-rays and biocompatible and has the necessary properties with respect to elasticity, flexibility and deformability. This means that the balloon tube 41 is made of a material that is suitable for balloons and easily expandable, yet firm, wherein the material of the covering tube 43 offers sufficient flexibility and withstands the pressure that is intended to cause the balloons 7, 9 and 11 to expand.

In an exemplary embodiment of the invention not shown in the drawing, the balloon system 5 is surrounded by a second outer elastic balloon tube, which can be asymmetrically expanded by the individual balloons 7, 9, 11 in several locations, so that the outer skin of the balloon system extends everywhere without sharp edges in a balloon-like manner, whereby in particular easier cleaning and a better visual impression is obtained.

The invention claimed is:

1. An apparatus for displacing a hollow organ of a patient during catheter ablation for cardiac arrhythmias to avoid injury to the hollow organ, the apparatus comprising:
   a balloon system comprising an elastic balloon tube which can be asymmetrically expanded in the hollow organ to exert a displacement pressure on an inner surface of the hollow organ,
   a catheter shaft, coupled to the expandable balloon system, having at least one lumen and radially extending passages fluidly connected thereto configured to control asymmetrical expansion of the balloon system using a filling medium; and
   a covering tube extending over the elastic balloon tube and including radially extending cut-outs aligned with the passages, wherein the cut-outs comprise a distal cut-out, an intermediate cut-out and a proximal cut-out, which alternately point in opposite directions along a longitudinal axis of the catheter shaft;
   wherein the expandable elastic balloon tube covers the passages and defines a plurality of balloons extending transversely to the catheter shaft, wherein the balloons are expandable independently of one another by introducing the filler medium to the passages to expand the balloon tube outward through the cut-outs such that every balloon has a unique longitudinal position along the catheter shaft.

2. The apparatus of claim 1, wherein the apparatus is configured to displace an esophagus of a patient during the catheter ablation to avoid esophageal injuries.

3. The apparatus of claim 1, wherein the balloons are spaced equidistantly apart from one another in a direction axial the catheter shaft.

4. The apparatus of claim 3, wherein the balloons are disposed along a longitudinal axis of the balloon system and alternately point radially in opposite directions.

5. The apparatus of claim 1, wherein the balloons are disposed laterally with respect to a longitudinal axis of the balloon system, pointing in different directions.

6. The apparatus of claim 1, wherein the at least one lumen comprises a single lumen through which a filling medium can be supplied to a plurality of the balloons.

7. The apparatus of claim 1, wherein the at least one lumen comprises three lumens, which are each configured to connect to a syringe via a feed line, and which each open into one of three passages associated with a respective balloon extending laterally with respect to the catheter shaft.

8. The apparatus of claim 1, wherein the distal end of the covering tube is curved, wherein the direction of curvature points in the direction of two of the balloons.

9. The apparatus of claim 1, wherein the balloons comprise first and second balloons aligned with one another along a longitudinal axis of the balloon system and a third balloon positioned between the first and second balloons and being circumferentially offset from the first and second balloons.

10. The apparatus of claim 9, wherein a distal tip of the covering tube is curved in a direction towards the first and second balloons.

11. An apparatus for displacing a hollow organ of a patient during catheter ablation for cardiac arrhythmias to avoid injury to the hollow organ, the apparatus comprising:
- a catheter shaft including at least one lumen and radially extending passages fluidly connected thereto for receiving a filling medium, the passages being asymmetrically positioned about the shaft;
- a balloon system comprising an elastic balloon tube covering the passages; and
- a covering tube extending over the elastic balloon tube and including radially extending cut-outs aligned with the passages, wherein the cut-outs comprise a distal cut-out, an intermediate cut-out and a proximal cut-out, which alternately point in opposite directions along a longitudinal axis of the catheter shaft, the elastic balloon tube being expandable in response to supplying the filling medium to the passages to define balloons extending transversely from the catheter shaft and through the cut-outs in an asymmetric manner such that every balloon has a unique longitudinal position along the catheter shaft, the balloons being expandable in the hollow organ to exert a displacement pressure on an inner surface of the hollow organ.

* * * * *